United States Patent [19]

Owens et al.

[11] Patent Number: 4,605,594

[45] Date of Patent: Aug. 12, 1986

[54] CERAMIC ARTICLES HAVING A NONPOROUS CORE AND POROUS OUTER LAYER

[75] Inventors: Kenneth E. Owens, Lake Elmo; Robert A. Hatch, Maplewood, both of Minn.

[73] Assignee: Minnesota Mining and Manufacturing Company, St. Paul, Minn.

[21] Appl. No.: 638,859

[22] Filed: Aug. 8, 1984

[51] Int. Cl.$^4$ .............................................. D02G 3/00
[52] U.S. Cl. .................................. 428/373; 428/375; 428/392; 428/400; 428/402
[58] Field of Search ............... 428/373, 375, 392, 400, 428/402

[56] References Cited

U.S. PATENT DOCUMENTS

| | | | |
|---|---|---|---|
| 2,461,841 | 2/1949 | Nordberg | 49/79 |
| 2,491,761 | 12/1949 | Parker et al. | 41/42 |
| 2,713,286 | 7/1955 | Taylor | 88/82 |
| 3,709,706 | 1/1973 | Sowman | 106/57 |
| 3,760,049 | 9/1973 | Borer et al. | 264/57 |
| 3,778,132 | 12/1973 | Pinnow et al. | 350/96 WG |
| 3,779,784 | 12/1973 | Emslie | 106/300 |
| 3,793,041 | 2/1974 | Sowman | 106/57 |
| 3,795,524 | 3/1974 | Sowman | 106/65 |
| 3,856,706 | 12/1974 | Harrison et al. | 252/450 |
| 3,881,944 | 5/1975 | Beall et al. | 106/39.7 |
| 3,909,278 | 9/1975 | Johnson | 106/65 |
| 4,047,965 | 9/1977 | Karst et al. | 106/65 |
| 4,125,406 | 11/1978 | Sowman | 106/57 |
| 4,166,147 | 8/1979 | Lange et al. | 428/328 |
| 4,314,827 | 2/1982 | Leitheiser et al. | 51/298 |
| 4,349,456 | 9/1982 | Sowman | 252/317 |

FOREIGN PATENT DOCUMENTS 1445331 8/1976 United Kingdom .

Primary Examiner—Marion C. McCamish
Attorney, Agent, or Firm—Donald M. Sell; James A. Smith; David L. Weinstein

[57] ABSTRACT

Fired ceramic article, which exhibits a uniform, porous sheath and a core. The porous sheath or outer layer of the article can be filled with various infiltrates, e.g., catalysts, in order to provide the article with useful properties. The article can be prepared by treating a fired ceramic article with a leachant, e.g., hydrofluoric acid or a precursor thereof.

51 Claims, 8 Drawing Figures

CERAMIC ARTICLES HAVING A NONPOROUS CORE AND POROUS OUTER LAYER

BACKGROUND OF THE INVENTION

This invention relates to ceramic articles, such as fibers, and to a process for producing the same.

"High-technology ceramics"—also known as high-performance ceramics, engineering ceramics, technical ceramics, advanced ceramics, and structural ceramics, and distinct from such conventional ceramics as pottery, dinnerware, cement, building bricks, roof tiles, and window glass—have excellent mechanical properties under heavy stress, outstanding electrical and optical properties, and exceptional resistance to high temperatures and corrosive environments.

High-technology ceramic articles having a core and a sheath are known in the art. U.S. Pat. No. 4,125,406 (Sowman) discloses ceramic fibers having at least two distinct zones of composition and properties. One zone was the core of the fiber and the second zone was a sheath or skin which is formed on the fiber during firing. U.S. Pat. No. 3,778,132 (Pinnow et al) discloses a transmission line structure having a core section made of pure amorphous silica and an encompassing section made of boron oxide ($B_2O_3$) admixed with silica which may be applied as a single layer cladding. U.S. Pat. No. 3,779,784 (Emslie) discloses fibers having a leachable core of alkali metal hexatitanate encapsulated by a shell of rutile ($TiO_2$); the fibrous material is particularly useful in reinforcing plastics.

U.S. Pat. No. 3,881,944 (Beall et al) discloses glass-ceramic articles demonstrating very high refractoriness, i.e., having a use temperature of at least 1,200° C. and a low coefficient of thermal expansion, i.e., less than $40 \times 10^{-7}$/°C. over the temperature range of 25°–900° C., which, when subjected to certain leaching treatments, will exhibit at least a surface layer manifesting a high and relatively uniform porosity with the vast majority of the pores having diameters ranging between about 0.1–40 micrometers to provide a surface area of about 1–100 meters$^2$/gram. Glass-ceramic bodies wherein a principal crystal phase is mullite, celsian, beta-spodumene, or cordierite can, in certain compositional areas, be leached to yield the above-described products. Hot dilute aqueous solutions of mineral acids such as HCl, $HNO_3$, $H_2SO_4$, $H_3PO_4$, etc., act to preferentially leach the celsian and cordierite crystals to yield porous bodies of high surface area but with extremely fine pores. Dilute aqueous solutions at room temperature (R.T.) of NaOH, HF, or $NH_4F:HF$ preferentially leach the beta-spodumene solid solution crystals to produce bodies with larger pores but also with much lower surface areas.

Although the foregoing patents describe products having useful properties, none of them describe an article with a capability of being filled or infiltrated with certain substances in a controlled geometry and in controlled amounts to render the article useful for applications previously considered unattainable. The article described in U.S. Pat. No. 3,778,132 is a glass article which is not designed for being infiltrated with substances. The article described in U.S. Pat. No. 3,779,784 would not be expected to be useful for infiltration applications. U.S. Pat. No. 4,125,406 describes an article which exhibits many desirable properties, but this patent does not describe infiltration of that article with high levels of substances. U.S. Pat. No. 3,881,944 does not in actuality describe a product having a core and a sheath; the patent does not indicate that the surface layer described therein has the ability to be filled with a high level of material.

SUMMARY OF THE INVENTION

This invention comprises, in one aspect, high technology ceramics which are fired, non-vitreous, monolithic, non-fused ceramic articles in various forms, e.g. unshaped and shaped articles such as fibers, cloths, beads, solid spheroids, and hollow spheroids, each such article having a geometrically uniform and microporous sheath or outer layer of high surface area at least partially covering or enveloping the core of the article. Such articles can be made by leaching precursor ceramic articles or preforms, e.g. sol-gel ceramics, with a leachant such as hydrofluoric acid.

As used herein, the term "ceramic" means a material made essentially from a refractory, nonmetallic, inorganic oxide material by firing at high temperatures. The term "core" means that central or inner portion of the ceramic article which is enveloped by a layer having a chemical composition different from that of the core. The term "sheath" or "outer layer" means the layer of said ceramic material having the configuration of a thin, porous case overlying or enveloping the core and contiguous therewith. The core can be substantially or completely encased by the contiguous sheath or outer layer or partially encased or covered therewith. The term "leaching" means the process of treating the outer surface of a shaped, fired ceramic article or preform by contacting the same with a liquid or gas which removes leachable or soluble components adjacent to the outer surface. The term "leachant" means the liquid or gas that is used to leach components from an unshaped or shaped, fired ceramic article. The term "leachate" means the solution of the soluble components in the leachant that is obtained by the leaching process.

The pores of the porous sheath or outer layer of the ceramic article can be filled with various fill materials in order to provide the ceramic article with desirable and useful properties. As used herein, the term "fill material" means any substance that can be made to accumulate in or fill the pores of the outer layer of the ceramic article whether it be in the form of a solid or fluid (i.e. liquid or gas). Certain fill materials in liquid form can be introduced into the pores of the outer layer of the ceramic article and then converted to solid form in situ, for example, by drying the liquid-filled outer porous layer.

The ceramic articles of the present invention can be prepared by contacting a fired ceramic article of the desired shape, e.g., a fiber, a bead, with a leachant, e.g., hydrofluoric acid, until a porous sheath or outer layer is formed on the unchanged ceramic core, and recovering the leached ceramic article.

The ceramic articles of the present invention can be modified by filling the porous sheath or outer layer with a fill material by treating the ceramic article with an infiltrate, e.g., a solution, dipersion, suspension, or the like, containing or comprising the desired fill material or precursor thereof, and recovering the infiltrated ceramic article. The infiltrated ceramic article optionally can be dried, heated, or fired in an oxidizing, neutral or reducing atmosphere in order to convert the fill material to a desired form.

Depending on the infiltrate, fill material, and ceramic used to make the ceramic article, and the shape and size thereof, the leached, filled ceramic articles of this invention can be used, for example, as supports for catalysts or enzymes, filter devices for use in high temperature environments, and fibers for magnetic, optical, and reinforcing applications.

DETAILED DESCRIPTION

Figure 3:
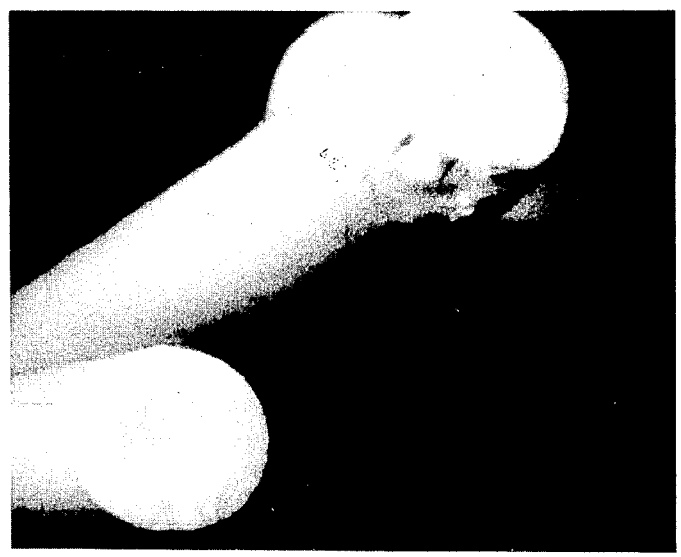
FIG. 3 is a picture of a fiber photographed at 2,500× using a scanning electron microscope prepared by leaching a fiber like that of FIG. 1 for 15 minutes at 22° C. in a 10% aqueous solution of hydrofluoric acid.

The ceramic articles of the present invention are non-vitreous, non-fused, monolithic articles characterized by having differential porosity and differential composition between the sheath or outer layer and the core, the latter being relatively non-porous (see FIG. 3). The surface of the ceramic article can be described as pebbly (see FIG. 4), that is, irregular, crinkled, or grainy.

The character of the core and sheath or outer layer can be visualized by the well-known techniques of scanning electron microscopy (SEM) with X-ray dispersive analysis capabilities and scanning transmission electron microscopy (STEM) wherein the surface of the leached ceramic can be examined or analyzed for contour and surface details and for chemical composition. The image obtained by STEM can be magnified or enlarged and visualized up to 100,000×. This allows one to visualize structural and chemical details of the surface, core, and sheath or outer layer down to about 50 Angstrom units, A. The geometry or boundary between the outer layer and the core is discrete and smooth and follows or is the same as the original surface, contour, or outline of the article prior to leaching and is displaced inward from that surface at a substantially uniform depth. The outer layer thus has a substantially uniform thickness. The thickness of the sheath or outer layer of a leached ceramic article can be from less than one micrometer to several micrometers, depending upon the conditions of preparation. For many ceramic articles of this invention, e.g. fibers, the average thickness of the sheath or outer layer can be 1/10 to 9 times the average thickness of the core. In some cases, the sheath or outer layer can have an average thickness greater than 9 times the average thickness of the core or an average thickness less than 1/10 times the average thickness of the core. Such factors as firing temperature and composition of the original ceramic articles can also have an effect on the thickness of the outer layer. The size of the ceramic article and the thickness of the sheath or outer layer can be measured by means of an optical microscope at suitable magnification (e.g. 400×).

The pores of the sheath or outer layer can be described as micropores, said micropores generally having an average diameter of less than 300 Å. Pores of this size are not discernible with an optical microscope at 500× but are discernible with a scanning transmission electron microscope at 100,000×. The micropores are interconnected and accessable from the leached article's periphery. The surface area of the sheath or outer layer varies with the shape or geometry of the article, but generally ranges from about 0.5 $m^2/g$ to about 100 $m^2/g$ in the case of a fiber. The core is relatively non-porous; the surface area of the core is generally from about 0.03 $m^2/g$ to about 0.2 $m^2/g$ in the case of a fiber. In general the ratio of the porosity of the sheath or outer layer to the porosity of the core is at least about 2.5:1 and is usually higher.

The ceramic articles of the present invention can be prepared by a leaching process wherein a ceramic article is treated with a chemical, e.g., hydrofluoric acid or precursor thereof, to separate and remove components of the ceramic article that react with, and may be soluble in, that chemical.

Ceramic materials amenable to chemical leaching according to the process of this invention include non-vitreous, non-fused ceramic articles having two or more phases wherein at least one phase has a low resistance to chemical attack by reactive solutions when compared to that of another phase or phases, both chemically resistant and chemically non-resistant phases being mutually interpenetrating so that a chemically resistant structure remains after the less-resistant phase is attacked. Fired ceramic articles in the shape of hollow spheroids, solid spheroids, fibers, beads, coatings, fabrics, flakes etc. and unshaped granules and aggregates that can be leached according to this invention are well-known in the art and are described in U.S. Pat. Nos. 3,709,706, 3,793,041, 3,795,524, 4,047,965, 4,125,406, 4,166,147, 4,349,456, 4,314,827, all of which are incorporated herein by reference (See FIG. 1 and FIG. 2). A preferred class of ceramic articles are shaped articles of the high-performance type having at least one dimension, e.g. diameter or width, discernible only upon magnification, e.g with an optical microscope at 400×.

Ceramic materials which are particularly susceptible to chemical leaching according to this invention are those obtained by sol-gel processes. These processes are thoroughly described in the previously noted U.S. Pat. No. 3,795,524. A typical sol-gel process involves shaping and converting a colloidal dispersion or hydrosol (sometimes called a sol) in a mixture with solutions or other sol precursors to a gel or any other physical state which restrains the mobility of the components, and then drying and firing the gelled, shaped article to obtain a ceramic material. A sol can be prepared by precipitation of a metal hydroxide from an aqueous solution followed by peptization, dialysis of anions from a solution of metal salt, solvent extraction of an anion from a solution of a metal salt, hydrothermal decomposition of a solution of a metal oxide or precursor thereof and is transformed to a semi-rigid solid state of limited mobility such as a gel by e.g., partial extraction of the solvent. Sol-gel processes can be employed to produce ceramic materials such as fibers, films, flakes and microspheres. Ceramic materials that are suitable for the present invention include the following mixtures of oxides:

alumina-silica
alumina-boria-silica
alumina-zirconia-silica
alumina-titania-silica
zirconia-silica
zirconia-boria-silica
zirconia-chromia-silica
zirconia-titania-silica
alumina-zirconia Representative examples of commercially available ceramics suitable for use in the present invention include alumina-containing ceramics designated by the trademarks NEXTEL®, available from Minnesota Mining and Manufacturing Company and SAFFIL®, available from ICI Ltd.

Chemical leachants that can be used to prepare the leached ceramic fibers of the present invention are hydrofluoric acid or precursors of hydrofluoric acid. Representative examples of leachants suitable for preparing the leached ceramic fibers include: hydrofluoric acid; mixtures of hydrofluoric acid and inorganic and/or organic acids, e.g. hydrochloric acid, acetic acid; and mixtures of fluoride salts, e.g. sodium fluoride, ammonium fluoride, and inorganic and/or organic acids, e.g. hydrochloric acid, acetic acid. Hydrofluoric acid, when used alone or with another acid, can be dissolved in either water or in non-aqueous solvents, e.g. ethanol, methanol, isopropanol, and mixtures thereof. In addition, hydrofluoric acid vapor can also be used as a leachant.

The concentration of the leachant, duration of the leaching process, temperature of the leaching process, and firing temperature of the ceramic article itself can be varied so as to obtain the desired degree of leaching, and, consequently, thickness of the sheath or outer layer.

An optical technique that can be used to determine whether a ceramic article has been leached to the desired degree, e.g., leached to leave a sheath, leached completely, leached not at all, is known as the Becke line method. This method is described in E. M. Chamot and C. W. Mason, *Handbook of Chemical Microscopy*, Vol. 1, 2nd ed., (Wiley:New York), 1938, Chapter XI. If one uses this technique, a complete leaching of the ceramic is made apparent by a difference in the index of refraction throughout the entire ceramic article. If a sheath is formed, it will have refractive index different from that of the core. If no leaching has occurred, there is no change in the index of refraction of the article. The greater the difference in index of refraction of the infiltrated index liquid used and that of the leached material, the greater the differentiation and visibility between the sheath or outer layer and core of the ceramic article.

According to this invention, mullite-type ceramic articles, e.g. fibers, of the composition $3Al_2O_3:2SiO_2$ can be fired at different temperatures and then leached with an acid, such as hydrofluoric acid. Articles fired at a temperature below that which causes complete conversion to mullite will undergo leaching whereas articles fired at a temperature of 1200°–1300° C. for sufficient time to convert to mullite will not undergo leaching. The formation of true mullite can be confirmed by X-ray analyses.

Leaching of ceramic articles containing more than two inorganic oxide components, such as alumina-boria-silica articles, to provide articles having a sheath or outer layer can also be carried out according to this invention. Unfired, air-dried alumina-boria-silica fibers ($3Al_2O_3:B_2O_3:2SiO_2$), prepared according to U.S. Pat. No. 3,795,524, can be fired at temperatures ranging from 800° C. to 1400° C., and leached with aqueous hydrofluoric acid; these three-component ceramic articles can be fired at relatively high temperatures, e.g. 800°–1400° C., so that they will not be dissolved by the leachant. Multicomponent articles fired below about 850° C., i.e., materials which have not yet attained microcrystalline properties, can be dissolved completely in the leachant.

Alumina-boria-silica articles can be leached to give a sheath or outer layer or can be completely leached, depending on such variables as firing temperature of the ceramic article, concentration of the leachant, duration of the leaching process, and temperature of the leaching process.

Leaching of three-component ceramic articles is also applicable to alumina-chromia-silica ceramics. Unfired, air dried $3Al_2O_3:Cr_2O_3:3SiO_2$ fibers, prepared according to U.S. Pat. No. 4,125,406 can be fired at various temperatures and leached with varying concentrations of aqueous hydrofluoric acid at varying temperatures for varying periods of time to give fibers having a sheath.

In the prior art, leaching generally involves the destruction of the integrity of the leach-resistant phase, wherein the composition of the ceramic is changed completely. The mode of leaching of this invention, in contrast, involves the dissolution of the readily leachable phase, leaving intact the leach-resistant phase. In the case of ceramics containing boria, silica, alumina, zirconia, the leach-resistant phase will be rich in alumina or zirconia, and the leachable phase will be rich in silica or boria. In the case of alumina-zirconia articles, the leach-resistant phase is the alumina-rich phase, and the leachable phase is the zirconia-rich phase. The ceramic articles of the present invention contain at least one crystalline or microcrystalline phase. The patents previously incorporated by reference describe ceramic materials with varying percentages of leach-resistant and leachable components.

Figure 7:
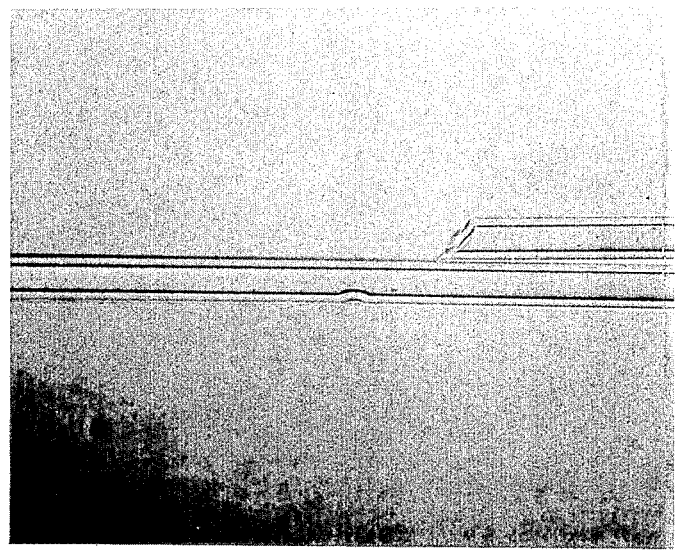
FIG. 7 is a picture of leached fibers, obtained by firing at 1000° C. fibers comprising $3Al_2O_3:B_2O_3:3SiO_2+2\%\ Cr_2O_3$ and leaching said fired fibers for 20 minutes at 22° C. in a 9.6% aqueous solution of hydrofluoric acid, said picture being that obtained by photographing said fibers with an optical microscope at 500× with transmitted visible light using a green filter.

Upon undergoing the leaching process described herein, transparent, non-vitreous ceramic articles, such as fibers, can be expected to retain their transparency, unlike glass, which would become opaque or translucent upon being similarly treated (see FIG. 7). For some particular applications, for example where the product is used as a reinforcement for composites, transparency will not be important. The transparent quality of a refractory product of this invention is coincident with other desirable properties, such as strength and flexibility, and thus transparency can be considered in a sense as a gross measure of the quality of the refractory product. In some applications of the refractory products of this invention, e.g. where a fiber or bundle of fibers are used in fiber optics or where microspheres are used in reflective sign surfaces, transparency will be of special importance.

In describing products of this invention as "transparent", this term means that the particular article in question, when viewed under a microscope has the property of transmitting rays of visible light, so that bodies beneath the article, such as bodies of the same nature as the transparent article, can be clearly seen through the transparent article, the outline, periphery, or edges of bodies beneath being sharply discernible. "Opaque" articles, on the other hand, are those which are impervious to visible light and bodies beneath are obscured by opaque article and cannot be seen therethrough. The "translucent" articles are those which fall between transparent and opaque, and though translucent articles have the property of transmitting visible light to some degree, and therefore are somewhat or partly transparent, bodies beneath can be seen in a diffuse manner rather than in a clearly distinguishable or sharp manner. Sometimes, a mixture of these various types of products, though generally one will be present in a predominant amount, indicative of the true nature of the mixture, the other products present in minor amounts having their particular appearance due to incomplete firing at the desired temperature or due to overheating because of hot spots in the furnace.

Figure 8:
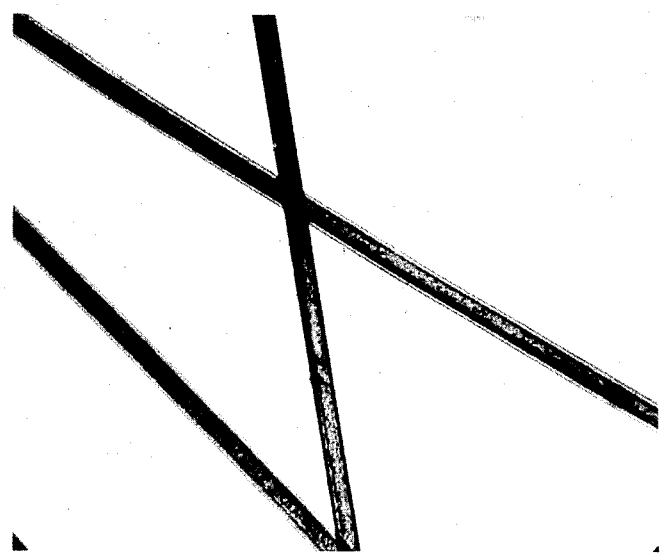
FIG. 8 is a picture of leached, filled, and fired fibers, obtained by leaching for 20 minutes at 22° C. in a 9.6% aqueous solution of hydrofluoric acid 900° C.-fired fibers of $3Al_2O_3:B_2O_3:2SiO_2$, infiltrating said leached fibers with a solution of chloroplatinic acid, and firing said infiltrated fibers to convert the chloroplatinic acid to platinum, said picture being that obtained by photographing the fired, filled fibers with an optical microscope at 625× with transmitted visible light.

Flexibility is another characterizing property of some of the refractory fibers of this invention. Flexible fibers in the form of monofilaments or in multifiber forms, e.g., threads, strands, yarns, rovings, tows, etc., are capable of being handled and fabricated, for example as flexible woven textiles or cloths, without breaking or other disintegration when bent or twisted, and in this application "flexibility" means that a plurality of fibers, e.g., 100, in the form of a tow or strand can be twisted to form a yarn or ties in the form of a "figure 8" knot without breaking. It is not essential in this invention to make the fibers with fine diameters in order to obtain flexibility, since fibers having diameters as large as 30 micrometers have been prepared with excellent flexibility.

Various ceramic forms such as fibers, both continuous fibers and non-continuous fibers, woven cloth, non-woven cloth, solid spheroids, hollow spheroids, flakes, and granules can be leached to provide ceramic articles having a core and a sheath. Regardless of the form of the ceramic article, e.g., a fiber or sphere, to be treated by this invention, leaching leads to a complete integral sheath or outer layer having substantially uniform thickness adjacent the periphery of that form. The ceramic article can also be in the form of a coating, i.e., the ceramic can first be coated on a substrate, then the exposed surface of the ceramic coating can be chemically leached, whereby said coating comprises a porous outer layer and a relatively non-porous inner layer.

As used herein, the term "continuous fiber" means a fiber (or monofilament) which has a length which is infinite for practical purposes as compared to its diameter, the latter dimension being only discernible upon magnification, e.g. with an optical microscope at 400×.

The continuous fibers of this invention can be as long as 10–20 feet, or longer. By bringing a plurality of the fibers together in the form of a continuous strand, tow, yarn, or other multifiber article, the occasional breakage or fracture of a continuous fiber does not affect the practical utility of the multifiber article containing a fiber whose length is relatively short. In any event, the fibers of this invention, even if broken or fractured, can be made in lengths which are significantly longer than the length of a staple fiber.

Uneven surfaces of chemical textiles made of ceramic fibers, or non-woven mats, for example, are particularly useful after the surface of the individual fibers have been modified by leaching according to the present invention. The resultant forms are useful for thermal protection, as for example, in heat resistant tiles for aerospace purposes. Thermal protection can be provided by two different mechanisms. One involves scattering and reflection of incident radiation, for example, infrared radiation, due to the greater number of optical interfaces introduced by controlled leaching. The second mechanism involves enhanced emissivity which is the result of leaching and suitable infiltration, and subsequent conversion to materials exhibiting high emission.

The ceramic material or product of this invention is refractory and generally particularly useful where high temperature stability or refractoriness is desired or required, for example up to and above 1000° to 1100° C. The refractory products of this invention can be employed alone or in various applications in the form in which they are obtained as fired, or their physical form can be modified, e.g., comminuted or pulverized to form a powder, or in their form as prepared as as modified they can be mixed or coated with or bonded to other materials, e.g. composite matrix materials.

The ceramic fibers of this invention are particularly useful in fabricating woven, non-woven, felted, knitted, and other types of textiles such as braids. Such textiles generally will have the same properties, such as high strength, flexibility, and refractoriness, as the fibers from which they are made. Fibers or yarns of this invention of different colors and/or composition can be used together in making fabrics with decorative designs. Some of these fibers, such as those containing ferric oxide as an internal colorant or additive, are capable of being branded to form designs thereon of different color. Fibers or yarns of this invention can be plied or interwoven with fibers of other materials, such as metal fibers, silica fibers, carbon, graphite, polytetrafluoroethylene (Teflon ®) or fiber glass, if desired. Woven cloths made from the refractory fibers can be firmly bonded as wall covering to various substrates. For example, such cloths can be bonded with molten glass, or refractory cements such as zircon, aluminum oxide, phosphates, and silicates, to aluminum or other metal substrates and used as the interior walls of airplanes. The woven cloths (or mats) can also be used as layups in plastic, metal, or ceramic laminates.

The ceramic fibers of this invention can be used in the form of fabrics, mats and batting as lightweight acoustical or thermal insulation for high temperature equipment, such as resistance and induction furnaces, and for purpose of heat shielding or reflecting, such as heating mantles and thermal curtains.

Because of their porous character, the ceramic fibers are useful in filtering or absorption applications, for example a filter to remove solids from hot gases, or as a chromatographic column packing to selectively separate or resolve liquids or gases, or as catalysts or catalyst supports.

Another particularly useful application for the ceramic products of this invention is that of reinforcement for structural plastic, elastomeric, metallic, or ceramic composites, especially those composites used in high temperature environments or even hyperthermal environments found in the aerospace industry, and in ablative environments. As composite reinforcement, the ceramic products of this invention are preferably used in the form of fibers (either in continuous or staple form), though other particulate forms, such as microspheres, aggregates, powders, and flakes, can be used for such purposes.

The ceramic fibers can be used to form fiber-reinforced plastic composites and fiber-reinforced metal matrix composites. The matrix materials which can be so reinforced include any of those heretofore used in making such composites, such as those disclosed in "Modern Composite Materials" edited by Brautman and Krock, published by Addison-Wesley Pub. Co., Reading, Mass. (1967). The plastics may be either of the thermosetting or thermoplastic types. Representative plastics which can be used include epoxy resins, polyester resins, acetal resins, acrylics, especially methyl methacrylate polymers, amino resins, especially urea-formadehyde, and melamine-formaldehyde, alkyds, cellulosics, especially ethyl cellulose, cellulose acetate, and cellulose proprionate, fluorocarbons, furanes, polyurethanes, phenolics, polyamides, polyimides, polycarbamates, vinyl aromatics such as styrene, polyolefins, especially polyethylene, and the like, and silicones. The ceramic fibers used as reinforcement for such plastics serve to strengthen shaped articles made from such plastics. Alternatively, in the form of particulate materials, ceramic products can be used as fillers and/or coloring agents or pigments for such plastics and for paints and enamels, such as water-based paints or alkyd-resin paints. The techniques which can be used in incorporating ceramic products of this invention as reinforcements in plastic matrices are well known, see "Handbook of Reinforced Plastics", by Oleesky and Mohr, Reinhold Pub. Corp., N.Y. (1964).

Metal matrix composites have had generally only limited application heretofore, one major reason being the lack of reinforcement materials which will withstand the elevated temperatures encountered in processing, e.g. casting and sintering temperatures. Ceramic products of this invention, because of their thermal stability, strength, flexibility and other properties, are useful as reinforcements, particularly in their fiber form, for metal composites, such as shaped or cast articles made of aluminum, copper, magnesium, nickel, titanium, zinc, lead, etc. Here too the prior art methods of incorporating reinforcements in metal matrix composites can be used, reference being made to "Fiber-Strengthened Metallic Composites", ASTM Spc. Tech. Pub. No. 427, published by the American Society for Testing and Materials, Philadelphia, Pa. (1967). Infiltrates can also be used to provide reinforcement for the ceramic articles.

Ceramic products of this invention can also be used as reinforcement for other ceramics, such as silica, glass, aluminum silicate, and other inorganic materials, such reinforced ceramics being in the form of felts, boards, blocks, paper, and other shaped articles used in high temperature environments.

Ceramic products of this invention can also be used as abrasion resistant and/or reinforcing agents (especially as fibers or in particulate form) for elastomeric materials, such as rubber, e.g. natural rubber, styrenebutadiene rubber (SBR), acrylonitrile-butadiene rubber (NBR), and neoprene (WRT), for example where such rubbers are used in making passenger-car or truck tires.

Figure 5:
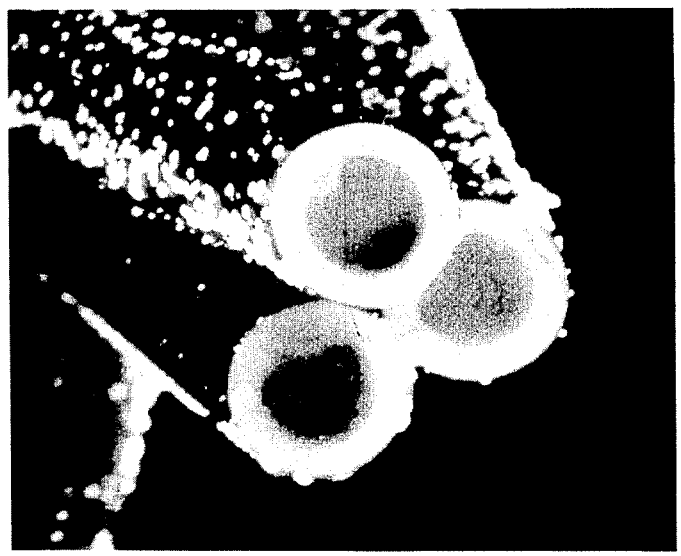
FIG. 5 is a picture of a fiber photographed at 2,500× using a scanning electron microscope prepared by infiltrating a leached fiber like that of FIG. 3 with a solution of chloroplatinic acid, and firing said infiltrated fiber to convert the chloroplatinic acid to platinum.

In addition to the foregoing, ceramic forms of this invention can be carrier supports, solid support material for chromatographic columns, and can be infiltrated with suitable fill materials to yield a variety of ceramic articles useful as oxidation and reduction catalysts. For example, ruthenium, platinum, palladium, copper chromite, silver, rhodium can be deposited within the pores of the sheath or outer layer of the ceramic article (see FIG. 5, FIG. 6, FIG. 8). Other fill materials include such materials as initiators, e.g. initiators of polymerization, inhibitors, e.g. oxidation inhibitors, antioxidants and the like, stabilizers, e.g. corrosion and degradation preventatives such as UV stabilizers. Biochemicals, e.g. enzymes, microorganisms, and materials derived from living or dead microorganisms can be immobilized in and on the porous sheath or outer layer of the ceramic article. Living microorganisms can also be immobilized in and on the porous sheath or outer layer.

Fill materials can also be employed to impart one or more of the following properties to the ceramic articles of this invention:

(a) magnetism;
(b) enhanced reflectivity/emissivity;
(c) altered index of refraction;
(d) rigidity, so that the ceramic articles can be used to reinforce elastomers and the like;
(e) altered surface tension, wettability, and bondability;
(f) enhanced electrical conductivity or resistivity;
(g) altered coefficient of friction.

The following non-limiting examples will further serve to illustrate the present invention. In all of the examples which follow, the index of refraction value of the sheath represents the value of the solid structural component only. The contribution to index of refraction from any fill material is excluded.

EXAMPLE 1

This example demonstrates the leaching of alumina-silica fibers. In each run, 0.064–0.104 g of $3Al_2O_3:2SiO_2$ fibers prepared in accordance with Example 2 of U.S. Pat. No. 4,047,965 were leached in 9.8% aqueous hydrofluoric acid for 15 minutes at room temperature (about 21° C.). Percentage of recovery was determined after the leachate had been decanted, the fibers rinsed with water several times, and their air dried at 100° C. for several hours. The results are shown in Table I.

TABLE I

| Sample no. | Unleached fiber | | Leached fiber[a] | | | |
|---|---|---|---|---|---|---|
| | Firing temperature (°C.) | Refractive index | Refractive index | | Sheath thickness (micrometers) | Recovery (%) |
| | | | core | sheath | | |
| 1 | 950 | 1.56–1.57 | 1.56–1.57 | 1.66 | 3–6 | 53 |
| 2 | 1100 | 1.54–1.55 | 1.56–1.57 | 1.67–1.68 | 1–4 | 67 |

TABLE I-continued

| Sample no. | Unleached fiber | | Leached fiber[a] | | | |
|---|---|---|---|---|---|---|
| | Firing temperature (°C.) | Refractive index | Refractive index | | Sheath thickness (micrometers) | Recovery (%) |
| | | | core | sheath | | |
| 3 | 1200 | 1.56–1.57 | 1.56–1.57 | 1.66–1.67 | 1–2 | 80 |
| 4 | 1300 | 1.62–1.63 | 1.63–1.64 | 1.63–1.64 | [b] | 60 |

[a]The fibers in sample nos. 1, 2, and 3 were crystalline alumina plus amorphous silica.
[b]The fiber was not leached. X-ray diffraction studies indicated that both unleached and leached fibers were leach-resistant mullite.

From Table I, it can be seen that fibers fired at 1300° did not undergo leaching, while fibers fired at temperatures below 1300° C. did undergo leaching.

EXAMPLE 2

Figure 1:
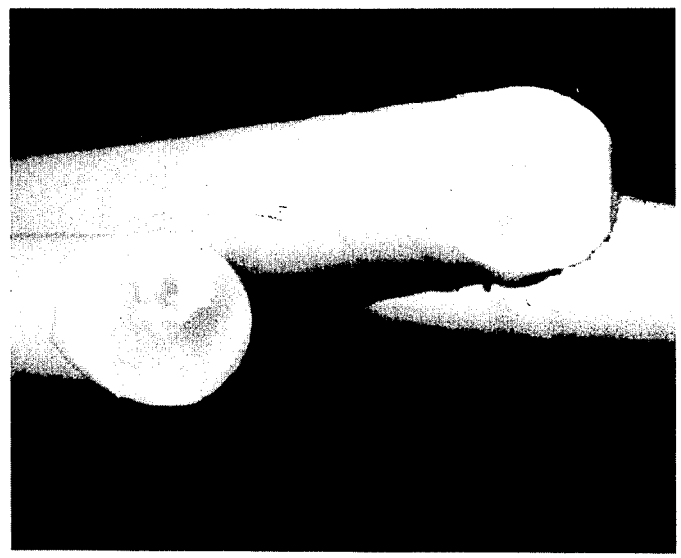
FIG. 1 is a picture of a ceramic fiber prior to leaching, photographed at 2,500× using a scanning electron microscope, said fiber obtained by firing at 1000° C. fibers comprising $3Al_2O_3:B_2O_3:2SiO_2$.
Figure 2:
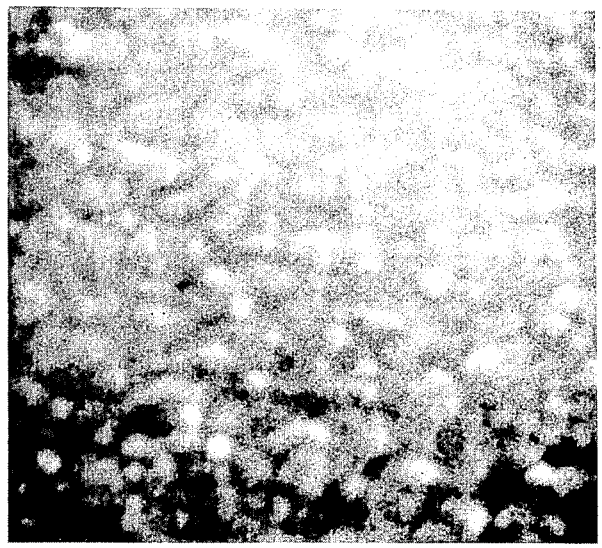
FIG. 2 is a picture of the peripheral surface of the fiber of FIG. 1 photographed at 100,000× using a scanning transmission electron microscope.
Figure 4:
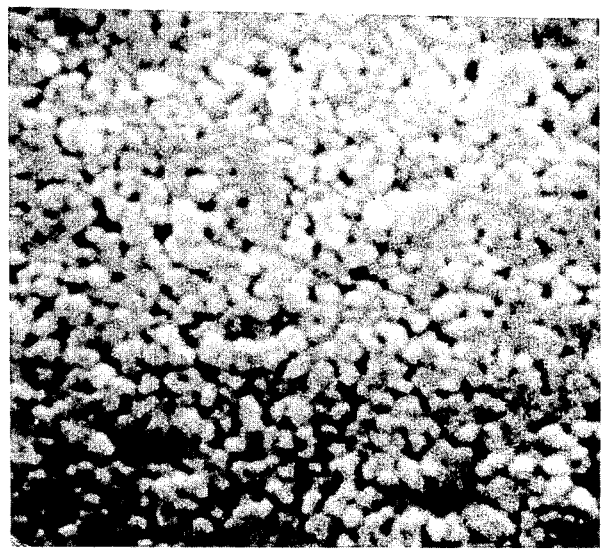
FIG. 4 is a picture of the peripheral surface of the fiber of FIG. 3 photographed at 100,000× using a scanning transmission electron microscope.

This example demonstrates the leaching of alumina-boria-silica fibers. In each run, 0.06–0.16 g of $3Al_2O_3$:$B_2O_3$:$2SiO_2$ fibers (as represented by FIG. 1 and FIG. 2) prepared in accordance with Example 10 of U.S. Pat. No. 3,795,524 were leached in aqueous hydrofluoric acid for 15 minutes at room temperature to give fibers as represented by FIG. 3 and FIG. 4. In runs 6,8–11, the concentration of hydrofluoric acid was 9.8%. In runs 5 and 7, the concentration of hydrofluoric acid was 9.6%. Percentage of recovery for this and succeeding examples was determined as in Example 1. The results are shown in Table II.

TABLE II

| Sample no. | Unleached fiber | | Leached fiber | | | |
|---|---|---|---|---|---|---|
| | Firing temperature (°C.) | Refractive index | Refractive index | | Sheath thickness (micrometers) | Recovery (%) |
| | | | core | sheath | | |
| 5 | 800 | — | — | — | — | complete disintegration[a] |
| 6 | 900 | 1.57–1.58 | 1.57–1.58 | 1.60–1.61 | 2 | 66 |
| 7 | 1000 | 1.57–1.58 | 1.57–1.58 | 1.61–1.62 | 2–4 | 67 |
| 8 | 1100 | 1.57–1.58 | 1.58 | 1.61–1.62 | 4–5 | 73 |
| 9 | 1200 | 1.57–1.58 | 1.61–1.62 | 1.61–1.62 | complete leach[b] | 68 |
| 10 | 1300 | 1.58–1.59 | 1.58–1.59 | 1.62 | 5–7[c] | 73 |
| 11 | 1400 | 1.58–1.59 | 1.59 | 1.62 | 5–6[c] | 91 |

[a]Fiber dissolved completely in leachant.
[b]Mixtures of mullite-like and mullite crystallites were present in the fibers as indicated by x-ray diffraction studies.
[c]Leach-resistant mullite remained as indicated by x-ray diffraction studies.

Fibers fired below about 850° C., i.e., materials which have not yet attained microcrystalline properties, were dissolved completely in the leachant. As the firing temperature of the unleached ceramic increased, the extent of leaching of the fired ceramic article also increased up to the point where volatization of boria occurs with consequent change in the chemical composition of the remaining fiber.

EXAMPLE 3

This example demonstrates the effect of leaching temperature on alumina-boria-silica fibers. In each run 0.15 g of $3Al_2O_3$:$B_2O_3$:$2SiO_2$ fibers were leached in 9.8% aqueous hydrofluoric acid for 15 minutes at the leaching temperature indicated. The results are shown in Table III.

TABLE III

| Sample No. | Firing temperature (°C.) | Leaching temperature (°C.) | Leached Fiber | | Recovery (%) |
|---|---|---|---|---|---|
| | | | Refractive index | | |
| | | | core | sheath | |
| 12 | 900 | 25 | 1.57–1.58 | 1.62 | 74[a] |
| 13 | 900 | 35 | 1.58–1.59 | 1.58–1.59 | 50[b] |
| 14 | 900 | 45 | 1.58–1.59 | 1.58–1.59 | 16[b] |
| 15 | 1100 | 25 | 1.60–1.61 | 1.60–1.61 | 56[b] |
| 16 | 1100 | 35 | 1.60–1.61 | 1.60–1.61 | 54[b] |
| 17 | 1100 | 45 | 1.60–1.61 | 1.60–1.61 | 8[b] |
| 18 | 1200 | 25 | 1.62 | 1.62 | 68[b] |
| 19 | 1200 | 35 | 1.62 | 1.62 | 81[b] |
| 20 | 1200 | 45 | 1.61–1.62 | 1.61–1.62 | 73[b] |

[a]Final fiber had sheath thickness of 1–2 micrometers.
[b]The fibers were leached completely.

From Table III, it can be seen that as the temperature of the leaching process increased, the extent of leaching increased dramatically.

EXAMPLE 4

This example demonstrates the effect of duration of leaching on alumina-boria-silica fibers. In each run, 0.12–0.15 g of $3Al_2O_3$:$B_2O_3$:$2SiO_2$ fibers were leached in 9.8% aqueous hydrofluoric acid at room temperature for the length of time indicated. The results are shown in Table IV.

TABLE IV

| Sample no. | Firing temperature (°C.) | Leaching time (minutes) | Leached fiber | | | |
|---|---|---|---|---|---|---|
| | | | Refractive index | | Sheath thickness (micrometers) | Recovery (%) |
| | | | core | sheath[b] | | |
| 21 | 900 | 1 | 1.57–1.58 | — | 0.5 | 73 |
| 22 | 900 | 5 | 1.57–1.58 | — | 2 | 80 |
| 23 | 900 | 15 | 1.57–1.58 | 1.61–1.62 | 2 | 66 |
| 24 | 900 | 60 | 1.57–1.58 | — | 2 | 27 |
| 25 | 900 | 90 | 1.57–1.58 | — | [a] | 0 |
| 26 | 900 | 120 | | | [a] | 0 |
| 27 | 1100 | 1 | 1.57–1.58 | — | 1–2 | 87 |
| 28 | 1100 | 5 | 1.58 | — | 2–3 | 80 |
| 29 | 1100 | 15 | 1.58 | 1.60–1.61 | 4–5 | 73 |
| 30 | 1100 | 60 | 1.60–1.61 | 1.60–1.61 | [a] | 33 |

TABLE IV-continued

| Sample no. | Firing temperature (°C.) | Leaching time (minutes) | Leached fiber | | Sheath thickness (micrometers) | Recovery (%) |
|---|---|---|---|---|---|---|
| | | | Refractive index | | | |
| | | | core | sheath[b] | | |
| 31 | 1100 | 90 | 1.61 | 1.61 | [a] | 7 |
| 32 | 1100 | 120 | 1.61 | 1.61 | [a] | 7 |

[a]The fibers were leached completely.
[b]The symbol "—" indicates that the refractive index was not measured.

From Table IV, it can be seen that as the duration of leaching increased, the extent of leaching increased. Given a sufficiently long period of time, complete leaching of the fiber occured.

EXAMPLE 5

This example demonstrates the effect of duration of leaching on alumina-boria-silica fibers when the leachant is dilute hydrofluoric acid. $3Al_2O_3:B_2O_3:2SiO_2$ fibers were leached in 0.98% aqueous hydrofluoric acid at room temperature for the length of time indicated. The fibers had previously been fired at 1100° C. The results are shown in Table V.

TABLE V

| Sample no. | Weight of sample (g) | Leaching time (hrs.) | Leached fiber | | Sheath thickness (micrometers) | Recovery (%) |
|---|---|---|---|---|---|---|
| | | | Refractive index | | | |
| | | | core | sheath | | |
| 33 | 0.37 | 0.5 | 1.57–1.58 | 1.61–1.62 | 0.5 | 81 |
| 34 | 0.28 | 2 | 1.58 | 1.62 | 4 | 75 |
| 35 | 0.43 | 19 | 1.57–1.58 | 1.61–1.62 | 4–6 | 2 |
| 36 | 0.23 | 19.25 | 1.61–1.62 | 1.61–1.62 | [a] | 43 |

[a]The fibers were leached completely.

From Table V, it can be seen that as the duration of leaching increased, the extent of leaching increased. Ultimately, complete leaching of the fiber occurred.

EXAMPLE 6

This example demonstrates the effect of concentration of leachant on the leaching of alumina-boria-silica fibers. In each run, 0.15 g of $3Al_2O_3:B_2O_3:2SiO_2$ fibers were leached for 15 minutes at room temperature with aqueous hydrofluoric acid leachant at the indicated concentration. In sample no. 37, 1.52 g of $3Al_2O_3:B_2O_3:2SiO_2$ were used. The results are shown in Table VI.

TABLE VI

| Sample no. | Firing temperature (°C.) | Leachant concentration (%) | Refractive index measurements | | | Leached fiber | Recovery (%) |
|---|---|---|---|---|---|---|---|
| | | | Before leach | After leach | | Sheath thickness (micrometers) | |
| | | | | core | sheath[d] | | |
| 37 | 1200 | 9.8 | 1.57–1.58 | 1.61–1.62 | 1.61–1.62 | [a] | 68 |
| 38 | 1200 | 0.98 | 1.58 | — | — | <1 | 87 |
| 39 | 1200 | 0.098 | 1.58 | 1.58 | | [b] | 100 |
| 40 | 1300 | 9.8 | 1.58–1.59 | 1.58–1.59 | 1.61–1.62 | 5–7 | 73 |
| 41 | 1300 | 0.98 | 1.58–1.59 | — | — | <1 | 73 |
| 42 | 1300 | 0.098 | 1.57–1.58 | 1.57–1.58 | | [b] | 73 |
| 43 | 1400 | 9.8 | 1.58–1.59 | 1.59 | 1.62 | 5–6[c] | 91 |
| 44 | 1400 | 0.98 | 1.58–1.59 | 1.58–1.59 | 1.62 | 1–2 | 91 |
| 45 | 1400 | 0.098 | 1.58–1.59 | — | — | <1 | 91 |

[a]The fibers were leached completely
[b]The fibers were leached not at all
[c]Approximately one-half the fibers were leached completely; the remaining fibers exhibited a thick leached layer with a thin, unaltered core.
[d]The symbol "—" indicates that the refractive index was not measured.

Fibers fired at 1200° C. and 1300° C. were not substantially leached by very dilute hydrofluoric acid. Fibers fired at 1400° C. were leached somewhat by very dilute hydrofluoric acid. This phenomenon can be explained by the probability that fibers fired at 1400° C. have lost a considerable amount of boria by volatilization and some residual prorosity may have been present, contributing to penetration of acid.

EXAMPLE 7

This example demonstrates the effect of form of the ceramic article on the leaching process. In each run, alumina-boria-silica forms were leached at room temperature under the conditions indicated. The results are shown in Table VII.

TABLE VII

| Sample no. | Unleached form | | | | Leaching Conditions | | Refractive index[e] | Leached form | | | Recovery (%) |
|---|---|---|---|---|---|---|---|---|---|---|---|
| | Form of ceramic | Ratio of alumina: boria: silica | Firing temperature (°C.) | Weight (g) | Leachant (%) | Duration (min) | | Refractive index | | Sheath thickness (micrometers) | |
| | | | | | | | | core | sheath[e] | | |
| 46 | Fiber | 3:1:3 | 1000 | 0.15 | 9.6 | 15 | — | [a] | | 2 | — |
| 47 | Fiber | 3:1:3[b] | 1000 | 0.15 | 9.6 | 15 | 1.57 | [a] | | 1–2 | — |
| 48 | Fiber | 3:1:3[c] | 1000 | 0.15 | 9.6 | 15 | 1.57 | [a] | | 1–2 | — |
| 49 | Cloth | 3:1:3 | 850 | approx 2 | 0.96 | 15 | — | [a] | | <1 | — |

TABLE VII-continued

| | | Unleached form | | | | | Leached form | | | |
|---|---|---|---|---|---|---|---|---|---|---|
| | | Ratio of alumina: boria: silica | Firing temperature (°C.) | Weight (g) | Leaching Conditions | | Refractive index[e] | Refractive index | | Sheath thickness (micrometers) | Recovery (%) |
| Sample no. | Form of ceramic | | | | Leachant (%) | Duration (min) | | core | sheath[e] | | |
| 50 | Cloth | 3:1:3 | 850 | approx 2 | 0.96 | 30 | — | [a] | | 1 | — |
| 51 | Cloth | 3:1:3 | 850 | approx 2 | 4.8 | 30 | — | [a] | | 1 | — |
| 52 | Microsphere (15)[d] | 3:1:5 | 950 | 20 | 0.96 | 25 | 1.5 | [a] | | ≦1-2 | 90 |
| 53 | Microsphere (10)[d] | 3:1:5 | 950 | 0.21 | 9.6 | 15 | 1.5 | [a] | | 1-2 | — |
| 54 | Microsphere (7-50)[d] | 3:1:4 | 1000 | 0.23 | 9.8 | 15 | 1.55-1.56 | 1.62-1.63 | | 2-4 | 52 |
| 55 | Microsphere (7-50)[d] | 3:1:4 | 1000 | 0.23 | 19.6 | 15 | 1.55-1.56 | 1.55 | 1.62 | 2-4 | 37 |
| 56 | Microsphere (10-50)[d] | 3:1:4 | 900 | 0.30 | 9.8 | 15 | 1.54-1.55 | 1.54-1.55 | 1.62-1.63 | 1-2 | 49 |
| 57 | Granules (250-1410)[d] | 3:1:2 | 600 | 2.00 | 0.96 | 30 | 1.57 | >1.57 | | 7-8 | 85 |
| 58 | Granules (250-1410)[d] | 3:1:5 | 600 | 2.00 | 0.96 | 30 | — | [a] | | | 85 |
| 59 | Granules (250-1410)[d] | 3:1:10 | 600 | 2.00 | 0.96 | 30 | — | [a] | | | 94 |

[a]The ceramic body was leached completely.
[b]The ceramic contained 2% $Cr_2O_3$.
[c]The ceramic contained 10% $Cr_2O_3$.
[d]Average diameter or range of diameter in micrometers is shown in parentheses.
[e]The symbol "—" indicates that the refractive index was not measured.

From the foregoing table, it can be seen that independent of geometric form, the leaching process of this invention resulted in a complete, integral sheath around that form.

EXAMPLE 8

This example demonstrates the leaching of alumina-chromia-silica fibers. In each run, 0.15 g of $3Al_2O_3$:$Cr_2O_3$:$3SiO_2$ fibers prepared according to Example 10 of U.S. Pat. No. 4,125,406 were leached for 15 minutes at room temperature with aqueous hydrofluoric acid leachant at the concentration indicated. The results are shown in Table VIII.

As the firing temperature of the given ceramic fiber increased, the fired ceramic fiber became more resistant to the leaching process. At the higher firing temperatures, recovery of material is greater, and there occurs transformation of a completely leached fiber to a sheathed, leach-resistant fiber.

EXAMPLE 9

This example demonstrates the effect of leaching temperature on alumina-chromia-silica fibers. $3Al_2O_3$:$Cr_2O_3$:$3SiO_2$ fibers were leached for 15 minutes with 9.8% aqueous hydrofluoric acid at the temperature indicated. The results are shown in Table IX.

TABLE VIII

| | Unleached Fiber | | | Leached Fiber | | | |
|---|---|---|---|---|---|---|---|
| Sample no. | Firing temperature (°C.) | Leachant concentration (%) | Refractive index | Refractive index | | Sheath thickness (micrometers) | Recovery (%) |
| | | | | core | sheath | | |
| 60 | 800 | 9.6 | 1.63-1.64 | 1.86-1.90 | 1.86-1.90 | [a] | 13 |
| 61 | 900 | 9.6 | 1.66-1.67 | 1.80-1.82 | 1.80-1.82 | [a] | 27 |
| 62 | 1000 | 9.6 | 1.67 | 1.80 | 1.80 | [a] | 47 |
| 63 | 1100 | 9.8 | 1.69-1.70 | 1.82 | 1.82 | [a] | 60 |
| 64 | 1200 | 9.8 | 1.69-1.70 | 1.84-1.86 | 1.84-1.86 | [a] | 60 |
| 65 | 1300 | 9.8 | 1.71-1.72 | 1.72-1.73 | 1.84-1.86 | 1-2 | 87 |
| 66 | 1400 | 9.8 | 1.72-1.73 | 1.77-1.78 | 1.84-1.86 | 2-3 | 87 |

[a]The fibers were leached completely.

TABLE IX

| | Firing temperature (°C.) | Leaching temperature (°C.) | Weight (g) | Refractive index | | | Leached fiber | |
|---|---|---|---|---|---|---|---|---|
| Sample no. | | | | Before leach | After leach | | Sheath thickness (micrometers) | Recovery (%) |
| | | | | | core | sheath | | |
| 64 | 1200 | Room | 0.15 | 1.69-1.70 | 1.84-1.86 | 1.84-1.86 | [a] | 60 |
| 67 | 1200 | 35 | 0.13 | 1.68-1.69 | 1.84-1.86 | 1.84-1.86 | [a] | 43 |
| 68 | 1200 | 45 | 0.04 | 1.68-1.69 | 1.86 | 1.86 | [a] | 35 |
| 65 | 1300 | Room | 0.15 | 1.71-1.72 | 1.72-1.73 | 1.84-1.86 | 1-2 | 87 |
| 69 | 1300 | 35 | 0.13 | 1.71 | 1.71-1.72 | 1.86 | 0.5-2 | 84 |
| 70 | 1300 | 45 | 0.17 | 1.71 | 1.71-1.72 | 1.84-1.86 | 0.5-2 | 83 |
| 66 | 1400 | Room | 0.15 | 1.72-1.73 | 1.77-1.78 | 1.84-1.86 | 2-3 | 87 |

TABLE IX-continued

| Sample no. | Firing temperature (°C.) | Leaching temperature (°C.) | Weight (g) | Refractive index Before leach | After leach core | After leach sheath | Leached fiber Sheath thickness (micrometers) | Recovery (%) |
|---|---|---|---|---|---|---|---|---|
| 71 | 1400 | 35 | 0.11 | 1.72–1.73 | 1.84–1.86 | 1.84–1.86 | a | 63 |
| 72 | 1400 | 45 | 0.19 | 1.72–1.73 | 1.84 | 1.84 | a | 64 |

<sup>a</sup>The fibers were leached completely.

The data of Table IX show that the fibers were partially leached at room temperature, while they were completely leached at elevated temperatures.

EXAMPLE 10

This example demonstrates the effect of concentration of leachant on leaching of alumina-chromia-silica fibers. In each run, 0.15 g of $3Al_2O_3:Cr_2O_3:3SiO_2$ were leached for 15 minutes at room temperature with aqueous hydrofluoric acid at the concentration indicated. The results are shown in Table X.

TABLE X

| Sample no. | Firing temperature (°C.) | Leachant concentration (%) | Refractive index measurements Before leach | After leach core | After leach sheath | Leached fiber Sheath thickness | Recovery (%) |
|---|---|---|---|---|---|---|---|
| 63 | 1100 | 9.8 | 1.69–1.70 | 1.82 | 1.82 | a | 60 |
| 73 | 1100 | 0.98 | 1.69–1.70 | 1.75–1.76 | — | b | 80 |
| 74 | 1100 | 0.098 | 1.69–1.70 | 1.69 | — | b | 100 |
| 64 | 1200 | 9.8 | 1.69–1.70 | 1.84–1.86 | 1.84–1.86 | a | 60 |
| 75 | 1200 | 0.98 | 1.69–1.70 | 1.69–1.70 | — | <1 | 87 |
| 76 | 1200 | 0.098 | 1.69–1.70 | 1.68–1.69 | — | c | 100 |
| 65 | 1300 | 9.8 | 1.71–1.72 | 1.72–1.73 | 1.84–1.86 | 1–2 | 87 |
| 77 | 1300 | 0.98 | 1.71–1.72 | 1.72 | — | <1 | 100 |
| 78 | 1300 | 0.098 | 1.71–1.72 | 1.71–1.72 | — | <1 | 100 |
| 66 | 1400 | 9.8 | 1.72–1.73 | 1.77–1.78 | 1.84–1.86 | 2–3 | 87 |
| 79 | 1400 | 0.98 | 1.72–1.73 | 1.73–1.74 | — | <1 | 100 |
| 80 | 1400 | 0.098 | 1.72–1.73 | 1.72–1.73 | — | <0.3 | 100 |

<sup>a</sup>The fibers were leached completely.
<sup>b</sup>Portions of the fibers were leached completely.
<sup>c</sup>The sheath was too thin to determine its thickness.
<sup>d</sup>The symbol "—" indicates that the refractive index was not measured.

From the foregoing Table it can be seen that for a given temperature a higher concentration of leachant gives either complete leaching or a sheath of greater thickness.

EXAMPLE 11

This example illustrates that alumina boria fibers will not undergo leaching. In each run 0.04–0.06 g of $9Al_2O_3:2B_2O_3$ fibers were leached for 15 minutes at room temperature with aqueous hydrofluoric acid (9.8%). The results are shown in Table XI.

TABLE XI

| Sample no. | Firing temperature (°C.) | Unleached fibers Weight (g) | Unleached fibers Refractive index | Leached fibers Refractive index core | Leached fibers Refractive index sheath | Recovery (%) |
|---|---|---|---|---|---|---|
| 81 | 800 | 0.04 | 1.59–1.60 | 1.59–1.60 | 1.59–1.60<sup>a</sup> | 26 |
| 82 | 1000 | 0.06 | 1.61–1.62 | 1.61–1.62 | 1.61–1.62 | 86 |

<sup>a</sup>The fibers were not leached.

From Table XI, it can be seen that aluminum borate fibers did not undergo leaching.

EXAMPLE 12

This example demonstrates the effect of leachant on alumina-boria-silica fibers. $3Al_2O_3:B_2O_3:2SiO_2$ fibers, which had been fired to 1000° C., were leached at about room temperature (23° C.) for the durations and with the leachants indicated. The refractive index of each fiber prior to the leaching process was 1.57–1.58. The results are shown in Table XII.

TABLE XII

| Sample no. | Leachant composition<sup>a</sup> | Leaching time (min.) | Refractive index After leach core | Refractive index After leach sheath | Leached fiber Sheath thickness (micrometers) | Recovery (%) |
|---|---|---|---|---|---|---|
| 83 | 18.6% NH<sub>4</sub>F | 180 | 1.57–1.58 | 1.57–1.58 | 0 | 100 |
| 84 | 18.7% NH<sub>4</sub>F 7.3% HCl | 30 | 1.57–1.58 | 1.62 | 2 | 91 |
| 85 | 18.7% NH<sub>4</sub>F 7.3% HCl | 15 | 1.57–1.58 | 1.62–1.63 | 1–2 | 94 |
| 86 | 18.6% NH<sub>4</sub>F 20.0% HC<sub>2</sub>H<sub>3</sub>O<sub>2</sub> | 30 | 1.57–1.58 | 1.62 | 1–2 | 96 |
| 87 | 18.5% NH<sub>4</sub>F 20.0% HC<sub>2</sub>H<sub>3</sub>O<sub>2</sub> | 15 | 1.57–1.58 | 1.62 | 1 | 94 |
| 88 | 9.7% HCl 9.6% HF | 15 | 1.61–1.62 | | b | 57 |
| 89 | 9.6% HCl 0.98% HF | 15 | 1.57–1.58 | 1.61–1.62 | 1–2 | 97 |
| 90 | 9.6% HCl | 15 | 1.57–1.58 | 1.57–1.58 | 0 | 100 |
| 91 | 9.6% HNO<sub>3</sub> | 15 | 1.57–1.58 | 1.57–1.58 | 0 | 98 |
| 92 | 10.0% H<sub>3</sub>PO<sub>4</sub> | 15 | 1.57–1.58 | 1.57–1.58 | 0 | 100 |

TABLE XII-continued

| Sample no. | Leachant composition[a] | Leaching time (min.) | Refractive index After leach core | sheath | Leached fiber Sheath thickness (micrometers) | Recovery (%) |
|---|---|---|---|---|---|---|
| 93 | 9.6% $H_2SO_4$ | 15 | 1.57–1.58 | 1.57–1.58 | 0 | 96 |
| 94 | 9.6% HF | 90 | 1.58 | 1.63 | 3–4 | 73 |
| 95 | 9.6% HF | 60 | 1.58 | 1.63 | 1–2 | 89 |
| 97 | HF vapor over 49% aqueous HF | 1440 | 1.57 | 1.62–1.63 | 1–4 | 69 |
| 98 | HF vapor over 49% aqueous HF | 240 | 1.57 | 1.62–1.63 | 1–2 | 93 |

[a]Sample nos. 83–93 were aqueous solutions. Sample no. 94 was a solution wherein the solvent comprised 95% ethanol and 5% water. Sample no. 95 was a solution wherein the solvent comprised 90% ethanol, 5% methanol, 5% isopropanol.
[b]The fibers were leached completely.

From the foregoing Table, it can be seen that ammonium fluoride ($NH_4F$), hydrochloric acid (HCl), nitric acid ($HNO_3$), phosphoric acid ($H_3PO_4$), and sulfuric acid ($H_2SO_4$) will not, by themselves, leach unfused ceramics to provide the leached ceramic article of this invention. When ammonium fluoride is used in combination with an acid such as hydrochloric or acetic, the mixture thereof will leach unfused ceramics to provide a leached ceramic article. When hydrogen fluoride is used in combination with a second acid such as hydrochloric, the speed of the leaching process is increased relative to that of a leaching process containing only hydrogen fluoride. Sample nos. 97 and 98 show that hydrogen fluoride vapor will also leach unfused ceramics to provide leached ceramic articles of this invention.

EXAMPLE 13

This example illustrates a method used for leaching a ceramic fiber to form an article of this invention.

Green, air dried aluminum borosilicate (alumina-boria-silica) fibers (15.65 g), prepared as described in U.S. Pat. No. 3,795,524, were fired from room temperature to 900° C. and held at 900° C. for four hours in a temperature controlled electric furnace to give 6.50 g of ceramic fibers whose calculated composition, based on original ingredients, was $3Al_2O_3:B_2O_3:3SiO_2$.

A leaching solution of 10% aqueous hydrofluoric acid was prepared by adding to a one liter plastic beaker 398 ml of distilled water and 102 ml of 48% aqueous hydrofluoric acid. Ceramic fibers (1.51 g) were added to the beaker at room temperature (21° C.) with stirring. After a fifteen minute leach time, the mixture was diluted with distilled water and the washed fibers were allowed to settle for one minute. Supernatant liquid was decanted and the water washing operation was repeated four times with the first two settling times being one minute in duration followed by two settling times of five minutes in duration.

After an additional water rinse followed by a fifteen minute settling time, further followed by decanting, the residual ceramic fibers were dried at about 95° C. for about 18 hours to give 1 g of leached, dry fibers.

Randomly chosen unleached and leached fibers were examined under a light microscope at 400X magnification using petrographic techniques. Each unleached fiber was colorless, transparent, and uniform in diameter. Although the diameter of each fiber was constant, the range in diameter from fiber to fiber varied from 8 to 18 micrometers. There was no apparent birefringence. A fiber having a uniform leached sheath with a sharp or distinct boundary was easily discernable under microscopic examination. The leached sheath was uniform in relation to its axis and outer surface of the fibers. Thickness of the uniform, leached sheath was about two micrometers. The index of refraction by the Becke line method was 1.57 to 1.58 for the unleached core and 1.61 to 1.62 for the remaining solid components of the leached sheath. Unleached cores, while uniform in diameter, did vary in diameter from fiber to fiber.

Surface area measurements of these unleached and leached ceramic fibers using the Quantasorb instrument (Quantachrome Corp., Greenvale, N.Y. 11548) indicated a surface area of 0.12 and 10.23 $m^2/g$ respectively.

EXAMPLE 14

This example illustrates the use of a leached fiber as a catalyst support for platinum. The resulting platinum-containing fiber was used as an oxidation catalyst for the oxidation of hydrocarbons (propylene) and carbon monoxide to form carbon dioxide and water.

About 5 g of $3Al_2O_3:B_2O_3:2SiO_2$ fibers previously fired to 900° C. were fired in air to 600° C. to remove any protective sizing. The fibers were leached in 9.6% aqueous hydrofluoric acid at room temperature for 20 minutes, rinsed with water, decanted several times, and air dried. Petrographic microscopic examination of the fibers revealed formation of uniform sheaths having a thickness of 1.5 micrometers.

The above leached fibers were equilibrated at room temperature with a 10% aqueous solution of chloroplatinic acid (Matheson, Coleman and Bell, Norwood, OH.) for 3.5 hrs. The treated fibers were drained and air-dried to give orange colored fibers. They were then fired in air at 600° C. for 2 hours to give black colored fibers, resulting from the finely divided platinum metal.

Figure 6:
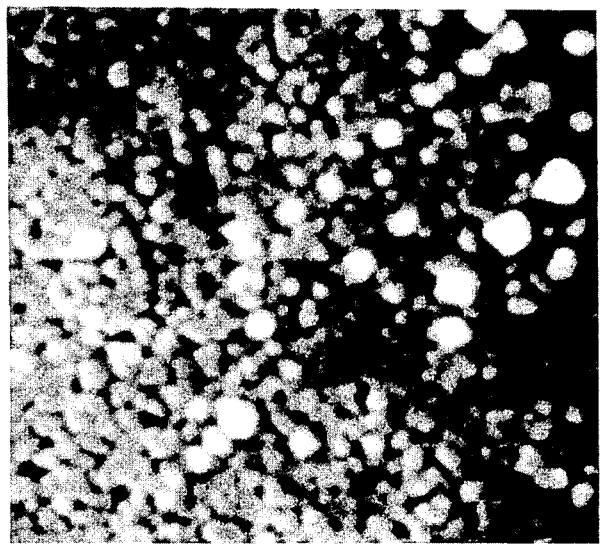
FIG. 6 is a picture of the peripheral surface of the fiber of FIG. 5 photographed at 100,000× using a scanning transmission electron microscope.

FIG. 6 shows microparticles of platinum (diameter ranging from 0.15 to 0.80 micrometers) distributed in a non-uniform manner along ceramic fibers of the present invention. The microparticles of platinum are the white dots residing in the lower right hand portion of the upper right hand quadrant. The dots are white because the lighting due to back-scattering techniques had to be altered to enhance the visibility of the platinum deposit on the photomicrograph.

Petrographic and scanning electron microscope examination revealed uniformly dispersed platinum on and in the leached sheath of the fiber.

The above platinum-containing fibers (4.4 g) were put into a stainless steel cartridge holder of dimensions 2.5 cm (1 in) diameter by 7.6 cm (3 in) long and a gas stream containing 1.0% carbon monoxide, 0.025% propylene hydrocarbon, 2.5% oxygen, about 10% water vapor, and the remainder nitrogen, flowing at the rate of 0.42 $m^3$/hr (15 $ft^3$/hr), was passed through the platinum-containing fibers as the temperature of the cartridge holder was raised from room temperature to about 500° C. over a period of about 10 minutes. Downstream analysis for carbon monoxide was performed by means of infrared analysis with a non-dispersive Beckman Model 315A infrared analyzer while downstream analysis for hydrocarbon was performed by means of a flame ionization detector with a Beckman Model 400 Hydrocarbon Analyzer. Excellent catalytic results were obtained for the oxidation of both carbon monoxide and hydrocarbons as exemplified by low light-off temperatures of carbon monoxide at 100° C. and propylene hydrocarbon at 125° C., with 100% conversion to carbon dioxide and water of the carbon monoxide at 230° C. and of the propylene hydrocarbon at 250° C. Light-off temperature is that temperature at which 5% conversion to carbon dioxide and water occurs.

EXAMPLE 15

This example illustrates the use of leached fibers, in the form of a woven fabric, onto and into which platinum has been deposited, for the catalytic reduction of p-nitrotoluene to p-toluidine.

Woven cloth formed from $3Al_2O_3:B_2O_3:2SiO_2$ fibers was leached and then infiltrated with 10% aqueous chloroplatinic acid ($H_2PtCl_6.6H_2O$) and dried at 100° C. The dry cloth was then fired in air for 1 hour at 600° C. in an electric furnace to give 1.06 g of a black fabric catalyst of dimensions 8 cm×4.5 cm.

Into an autoclave were placed the black fabric catalyst, 1 g of p-nitrotoluene (m.p. 51.2°-53° C., Matheson, Coleman and Bell, Gibbstown, NJ), and 10 ml of hexane. The autoclave was pressurized to $4\times10^5$ Pa (58 pounds per square inch) with hydrogen gas, and catalytic reduction was complete in less than one-half hour at room temperature. The autoclave was vented to remove hydrogen, and white flaky crystals deposited on and around the catalyst and within the autoclave were recovered. The crystals were collected by filtration and melted at 43.8°-44.8° C. (reported melting point for p-toluidine is 45° C.). Infrared spectroscopy and gas chromatography confirmed the reduction of p-nitrotoluene to p-toluidine. About 0.6 g of p-toluidine was recovered from the combined methanol rinses of the catalyst and autoclave and hexane solvents. The black fabric catalyst was completely recovered.

The remainder of this example describes the recycling of the recovered black fabric catalyst and its use to reduce more p-nitrotoluene to p-toluidine. Catalyst in this form is readily retrievable, i.e. it does not have to be removed by filtration from the reduction product.

Into a suitable autoclave were placed 1 g of p-nitrotoluene (m.p. 51.2°-53° C.; Matheson, Coleman and Bell, Gibbstown, NJ), 10 ml of hexane, and all of the recovered black fabric catalyst from the previous part of the example. The autoclave was pressurized to $3.6\times10^5$ Pa (53 pounds per square inch) with hydrogen gas, and catalytic reduction was complete in less than one-half hour at room temperature. The autoclave was vented to remove hydrogen, and white flaky crystals deposited on and around the catalyst and within the autoclave were recovered. The crystals were collected by filtration and melted at 44.2°-45.2° C. The melting point, 44.2°-45.2° C., was not depressed on admixture of the above white flaky crystals with a sample of p-toluidine whose structure had been previously confirmed by melting point and infrared spectroscopy.

EXAMPLE 16

This example illustrates the use of leached fibers, in the form of a woven fabric, onto and into which platinum has been deposited, for the catalytic dehydrogenation (oxidation) of dihydrobenzo[a]carbazole to 11-H-benzo[a]carbazole.

Into a suitable sized flask were placed 15 g of dihydrobenzo[a]carbazole (C. U. Rogers and B. B. Corson, *Organic Syntheses*, Coll. Vol. IV, N. Rabjohn, ed., Wiley Publishers, NY, 1963, p. 884), 50 ml of xylene (J. T. Baker Co., Phillipsburg, NJ), and about 0.5 g of unused black fabric catalyst (from Example 14). The mechanically stirred mixture was heated under reflux for about 29 hours. Upon cooling was deposited pure 11-H-benzo[a]carbazole, identified by infrared spectrum and its melting point (228°-230° C., reported melting point 228° C.; see I. Heilborn, *Dictionary of Organic Compounds*, Oxford University Press, NY, 1965, vol. 1, p. 339).

EXAMPLE 17

This example illustrates electroless nickel metal deposition onto leached ceramic fibers.

Leached $3Al_2O_3:B_2O_3:2SiO_2$ fibers prepared as in Example 13 (0.5 g, 11 micrometers in diameter and having a 2-3 micrometer thick uniform sheath) were infiltrated by immersing the fibers at room temperature for 5 minutes in a solution comprising 49.2 g of stannous chloride, 322.4 g of sodium chloride, 30.4 ml of 0.5 molar stannic chloride (aged), and 78.4 ml of concentrated hydrochloric acid diluted with distilled water to a volume of 1 liter. The solution was decanted, and the recovered fibers were then immersed at room temperature for 5 minutes in a solution containing 1 g of palladium(II) chloride and 1.7 g of concentrated hydrochloric acid diluted with distilled water to a volume of 1 liter. The fibers were recovered by decantation and then immersed at 85°-90° C. for 5 minutes in Sel-Rex Lectroless nickel solution (Sel-Rex Co., subsidiary of Hooker Chemical Corp., Nutley, NJ). The fibers were recovered and rinsed with distilled water and dried at 100° C.

Examination with a microscope (40 ×, reflected light) showed a uniform black shiny metallic coating on each individual fiber. Examination (100-400 ×) under transmitted light indicated 11 micrometer diameter, uniform coated opaque black fibers whose sheaths were not visible. The electrical conductivity of these fibers, as measured by a conventional ohmmeter, indicated a resistance of about 50 ohms at a 25.4 mm (1 in) separation of electrodes and a resistance of about 5 ohms at a 6.25 mm (0.25 in) separation of electrodes.

EXAMPLE 18

This example illustrates low melting metal reinforcement by means of electroless nickel-plated leached ceramic fibers.

Fibers as described in Example 17 (0.05 g) were mixed with 1.90 g of fine lead powder (Fisher Scientific Co., Fair Lawn, NJ), and fired in a ceramic boat.

Additional fibers as described in Example 17 (0.08 g) were mixed with zinc dust (Mallinckrodt Chemical Co., St. Louis, MO) and fired in a ceramic boat.

In each case, the firing was conducted for 1 hour at 580° C. in an atmosphere of 5% hydrogen and 95% argon. Microscopic examination (40×) showed bonding of the nickel coated fibers to lead and to zinc, respectively. At 300× and 750× magnification, the bonding of nickel to the zinc and lead, respectively, was confirmed. X-ray dispersive analysis and scattering electro microscopy (SEM) substantiated these observations.

EXAMPLE 19

This example illustrates the zinc nitrate infiltration of leached, sheathed ceramic fibers, which after firing, have an index of refraction greater than that of the ceramic core of a leached fiber not so treated and fired.

Partially leached $3Al_2O_3:B_2O_3:2SiO_2$ fibers (1.0 g) prepared as in Example 13 (11 micrometers in diameter having a 2-4 micrometer thick uniform sheath) were infiltrated by immersing the fibers at room temperature for one hour in a solution of 5 g of zinc nitrate hexahydrate in 100 ml of distilled water. The solution was drained from the fibers, which were then air dried for about 3½ hours at 100° C. The fibers were placed in a crucible and were fired in air in a program-controlled electric furnace which progressed from room temperature to the temperature indicated in Table XII within 2 hrs. One batch of fibers was fired at 600° C. (Batch 1). A second batch of fibers was fired at 600° C., cooled, reimmersed in the zinc nitrate solution, and refired at 600° C. (Batch 2). Batches 3 through 6 were fired at 800° C., 1000° C., about 1215° C. and about 1400° C., respectively. Physical properties of the resulting zinc oxide infiltrated fibers are set forth below:

TABLE XIII

| Batch[a] no. | Firing temperature (° C.) | Refractive index Sheath[b] | Core |
|---|---|---|---|
| 1 | 600 | 1.65 | 1.60 |
| 2 | 600 | 1.64–1.65 | 1.62–1.63 |
| 3 | 800 | 1.63 | 1.62–1.63 |
| 4 | 1000 | 1.63–1.64 | 1.60–1.61 |
| 5 | 1210–1218 | 1.63–1.64 | 1.62–1.63 |
| 6 | 1398–1406 | 1.69–1.70 | 1.67–1.68 |

[a]Diameters of fibers were 11 micrometers except for batch no. 6 whose diameters were 10–11 micrometers.
[b]Thickness of sheath was 2–4 micrometers for batches 1–5 and 2–3 micrometers for batch no. 6. Refractive index contribution by any infiltrate is excluded.

Fibers in batches 1–4 were clear, transparent, uniform and birefringent. Fibers in batches 5 and 6 had a general mottled appearance. As firing temperature increased, infiltration of zinc oxide into the sheath and its migration into the core and sheath increased.

EXAMPLE 20

This example illustrates the use of a leached fiber to absorb and immobilize an active enzyme. The resultant immobilized active enzyme readily promotes the decomposition of hydrogen peroxide to oxygen and water.

About 1 g of dry $3Al_2O_3:B_2O_3:2SiO_2$ fibers fired at 1016° C., leached in 10% aqueous hydrofluoric acid at room temperature (22° C.), and dried according to the method of Example 13 yielded fibers having a diameter of 11 micrometers with a uniform sheath of thickness 2–4 micrometers. The leached fibers were equilibrated at room temperature with 50 ml of distilled water.

Catalase enzyme C-10 (0.1 g, Sigma Chemical Co., St. Louis, MO) was equilibrated at room temperature with 50 ml of distilled water for 1 hr with mixing. The mixture was filtered to give a slightly opalescent light yellow filtrate.

Water was decanted from the above-mentioned water-equilibrated fibers. The catalase-containing opalescent light yellow filtrate was poured onto the sheathed fibers, and the resultant mixture was equilibrated for 4 hours. The liquid was decanted and the residual catalase enzyme supported on the leached ceramic fiber was rinsed with distilled water. The rinse water was then decanted. The washing procedure was repeated several times, and the fibers were allowed to dry at about 30° C. for several days to allow evaporation of excess water. The fibers, light yellow to buff in color, were kept moist for enzyme activity studies.

About 0.25 g of the above-mentioned enzyme-fiber complex was rinsed with distilled water, and the water was decanted. This rinsing operation was performed two additional times. Hydrogen peroxide (10 ml of 0.1% $H_2O_2$ solution) was added and the stirred mixture immediately evolved oxygen gas. The pH of this mixture at room temperature was 6.8. The mixture was tested with white potassium iodide-starch indicator test paper manufactured by Curtin Matheson. In the presence of oxidizing agents such as hydrogen peroxide, the indicator paper becomes blue-purple. Immediately after the addition of hydrogen peroxide, the indicator paper turned blue-purple. After 25 minutes, indicator paper turned to an extremely faint blue-purple, and after 40 minutes, indicator paper remained colorless, indicating that the immobilized enzyme completely decomposed hydrogen peroxide according to the equation:

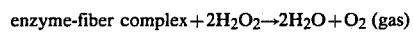

$$\text{enzyme-fiber complex} + 2H_2O_2 \rightarrow 2H_2O + O_2 \text{ (gas)}$$

The used enzyme-fiber complex from above was recovered by decantation and rinsed with 10 ml of distilled water which was then decanted. Hydrogen peroxide (10 ml of 1% hydrogen peroxide solution) was added with stirring and oxygen gas evolved at room temperature. The pH of the mixture was 6.8, and indicator paper turned blue-purple. After 15 minutes, the indicator paper became light blue-purple, and after 45 minutes, the indicator paper did not change color, indicating the complete decomposition of hydrogen peroxide.

In a similar experiment, enzyme-fiber complex (1 g) completely decomposed 10 ml of 6% hydrogen peroxide solution in 1.75 hrs as determined by the indicator paper method.

EXAMPLE 21

This example illustrates the use of covalently immobilized catalase enzyme on leached $3Al_2O_3:B_2O_3:2SiO_2$ fibers.

Dry leached fibers (1 g) prepared as in Example 13 were equilibrated with 50 ml of distilled water, and the fibers were then covalently bonded with catalase enzyme using 3-aminopropyltriethoxysilane-glutaraldehyde, according to the practice described in "Immobilized Enzymes, Antigens, Antibodies, and Peptides—Preparation and Characterization", H. H. Weetall, ed., Marcel Dekker, New York, 1975, p. 13. The resultant product was rinsed with distilled water followed by decantation several times to yield a light yellow to buff solid. The solid was maintained in a moist condition.

About 0.75 g of the moist product was rinsed with 10 ml of distilled water and the rinse was decanted. The rinsing procedure was performed two additional times. Ten ml of 0.1% hydrogen peroxide solution was added at room temperature. The pH of the mixture was 6.4. Catalytic decomposition was complete in 3.25 hrs., as determined by the indicator paper method.

EXAMPLE 22

This example compares leached ceramic fibers with unleached ceramic fibers, both in the form of woven tapes and cloths, with respect to reflectivity and emissivity.

Woven tape prepared from $3Al_2O_3:B_2O_3:2SiO_2$ fibers, 5.1 cm. (2 inch) wide, is a commercial product available from 3M, St. Paul, MN under the trademark "NEXTEL" 312 woven tape, WWS-2820. The control sample was fired at 1016° C. and had fibers of 11 micrometer diameter. A similar tape was fired at 1016° C. and leached in 10% aqueous hydrofluoric acid at room temperature for 15 minutes to give a woven tape having leached $3Al_2O_3:B_2O_3:2SiO_2$ fibers of 11 micrometer diameter with a uniform sheath 4 micrometers thick.

Woven cloth prepared from $3Al_2O_3:B_2O_3:2SiO_2$ fibers (8 harness satin, 40×40 warp and fill thread count) is a commercial product available from 3M, St. Paul, MN under the trademark "NEXTEL" 312 Woven Fabric 8 Harness Satin. The control sample was fired at 1000° C. and had fibers of 11 micrometer diameter. A similar cloth was fired at 1000° C. and leached in 10% aqueous hydrofluoric acid at room temperature for 15 minutes to give a woven cloth having leached $3Al_2O_3:B_2O_3:2SiO_2$ fibers of 11 micrometer diameter with a uniform sheath 2-3 micrometers thick.

Reflectivity/emissivity measurements were made on these tape and cloth samples using Emissometer Model AE using the RD-1 Scaling Digital voltmeter. A warmup time of about 2 hours was allowed. Scaling was made with the emission standards: Al sheet (E=0.04); black coating on Al sheet (E=0.93). Measurements were made at room temperature or slightly above. Wavelength range was 3 to 30 micrometers.

Leached woven tape had a reflectivity/emissivity ratio ranging from 4-6% (average of 5%) greater than that of the control woven tape.

Leached woven cloth had a reflectivity/emissivity ratio ranging from 1-13% (average of 9%) greater than that of the control woven cloth. The woven cloths were somewhat irregular and the two sides of the respective cloth were somewhat different after the weaving process, thus giving wider variability of results.

EXAMPLE 23

This example illustrates the high emissivity of leached ceramic fibers in the form of woven cloths wherein said cloths were infiltrated with aqueous solutions of inorganic materials prior to firing.

The leached woven cloth was the same type as that described in Example 22. Swatches (6.35 cm×3.81 cm) of the fired, leached cloth were infiltrated with an excess of an aqueous solution of inorganic materials as indicated below.

Sample 1 (0.83 g) was infiltrated with a 10% aqueous solution of $H_2PtCl_6.6H_2O$. The sample was then dried at 100° C. and fired in air at 600° C. to give black cloth (0.88 g) having uniformly deposited finely divided platinum.

Sample 2 (0.88 g) was infiltrated with a 6.1% aqueous solution of $Ni(NO_3)_2.6H_2O$. The sample was then dried at 100° C., fired in air at 600° C., and fired in a 5% hydrogen-95% argon atmosphere at 604° C. to give a black woven cloth (0.89 g) having uniformly deposited finely divided nickel.

Sample 3 (0.91 g) was infiltrated with an aqueous mixture comprising the following salts:

3.7%: $Cr(C_2H_3O_2)_3.H_2O$
3.0%: $Fe(NO_3)_2.9H_2O$
0.5%: $MnCl_2.4H_2O$
1.8%: $Co(NO_3)_2.6H_2O$
0.7%: $Ni(NO_3)_2.6H_2O$

The sample was then dried at 100° C. and fired in air at 600° C. to give a black woven cloth with a yellow tint (0.97 g) having uniformly deposited finely divided metal oxides. Reference to the conversion of inorganic salts and the like to metal oxides and metals can be found in "Ceramic Glazes" by C. W. Parmelee, Industrial Publications Inc., Chicago, IL, 1948, pp. 280–282.

Emissivity tests for samples 1 to 3 and for an unleached woven cloth control sample of the type as in Example 21 are set forth in Table XIV. Emissivity tests were made under the conditions described in Example 21.

TABLE XIV

| Sample | Emissivity (E) |
|---|---|
| 1 | 0.65–0.69 |
| 2 | 0.67–0.70 |
| 3 | 0.67–0.74 |
| Control | 0.56–0.60 |

EXAMPLE 24

This example compares leached ceramic fibers with unleached ceramic fibers, both in the form of woven cloths, with respect to thermal protection and infrared (IR) protection.

The leached woven cloth was identical to that described in Example 22 with the exception that leaching was performed in 9.8% aqueous hydrofluoric acid under the stated conditions to yield a cloth whose fibers were 11 micrometers in diameter and whose uniform sheath was 2 micrometers thick. A 4.52 g swatch having the dimensions 4.4 cm×38 cm was used. A similar, unleached swatch served as a control.

An electrically powered high temperature furnace with nichrome wire resistance heating element was used to heat and irradiate the test materials. The furnace was cylindrical in shape and the heat emanated from the periphery inward towards the test specimens. The furnace was insulated with pieces of insulating firebrick. A platinum/platinum-rhodium thermocouple placed at the center of the furnace on the axis of the cylindrical furnace recorded the temperatures inside of the test specimen assembly and on the side of the test material opposite to the furnace heating elements. A constant voltage was applied to the nichrome heating elements to start and maintain the test. Amperage and temperature were noted and recorded at regular time intervals, usually every five minutes. Typical operation was at 110 volts, 3.8 amperes, and 418 watts, with the temperature rising from room temperature to about 1200° C. in 2 hrs.

The ceramic woven fabric swatches were wrapped around a fine stainless steel screen (100 mesh, 80 micrometer) which had been formed into a cylinder 4.4 cm (1.75 in) in height and 3.8 cm (1.5 in) in diameter. Three layers of woven cloth were used in each case. The nichrome heating elements were approximately 0.32–0.64 cm (⅛–¼ in) from the surface of the ceramic woven fabric test specimens.

Using constant electrical power and comparable woven samples, the rise in temperature at the center axis on the opposite side of the test specimens from the nichrome furnace were recorded as a function of time.

The leached ceramic woven fabric specimen resulted in a lagging of the temperature as a function of time of 10° and 11° C. over the temperature ranges 24° to 978° C. and 22° to 1070° C., respectively, when compared with the unleached ceramic woven fabric specimen under identical conditions of geometry and power.

EXAMPLE 25

This example compares the index of refraction of leached ceramic beads in air with the index of refraction of unleached ceramic beads.

Two batches of $3Al_2O_3:B_2O_3:4SiO_2$ ceramic beads were prepared by the alcohol extraction process described in U.S. Pat. No. 4,166,147. One batch (batch A) was fired in air at 900° C. for 2 hours, and a second batch (batch B) was fired in air at 1000° C. for 1 hour.

A portion of each of the above two batches was leached in 9.8% aqueous hydrofluoric acid for 15 minutes at room temperature. The leached beads were then rinsed several times with distilled water and dried at 100° C. The beads were examined microscopically (100–400×) using standard index of refraction liquids by means of the Becke line method, which revealed a clearly visible, nonbirefringent, transparent, colorless, uniform leached layer (sheath) with a line of demarcation between the sheath and the core. The visible physical characteristics of the two leached batches are set forth in Table XV. Refractive index contribution by any infiltrant is excluded.

of the core was 1.61. The refractive index of the sheath was 1.67.

EXAMPLE 27

This example illustrates the use of $3Al_2O_3:B_2O_3:2SiO_2$ fibers to reinforce an elastomer.

Leached $3Al_2O_3:B_2O_3:2SiO_2$ fibers (0.75 g), in the form of a woven fabric as described in Example 15, were saturated by immersing the fabric in a solution of 1 g of Fluorel®223 elastomer (commercially available from Minnesota Mining & Manufacturing Co., St. Paul, MN) in 10 ml of acetone. The fabric was allowed to air-dry at room temperature for about one day.

Visual inspection of the fabric-reinforced Fluorel®223 elastomer revealed good impregnation and infiltration of the fiber. Microscopic examination (400×) showed a translucent polymer matrix. The leached sheath was clearly visible as the refractive index of Fluorel®223 is less than 1.40 and movement of the Becke line (petrographic technique) indicated that the infiltrated, leached sheath had an index of refraction less than that of the unaltered fiber core (about 1.57–1.58).

EXAMPLE 28

This example illustrates the infiltration of $3Al_2O_3:B_2O_3:2SiO_2$ ceramic fibers with a magnetic material to render the resultant product magnetic.

Leached $3Al_2O_3:B_2O_3:2SiO_2$ fibers as described in

TABLE XV

| | Unleached beads | | Leached beads | | |
|---|---|---|---|---|---|
| Batch | Diameter (Micrometers) | Index[a], of refraction | Thickness (Micrometers) | Index of refraction* | Composite bead index of refraction[b] |
| A | 8–70 | 1.55 | 1–2 | 1.62–1.63 | 1.61 |
| B | 10–50 | 1.55–1.56 | 2–4 | 1.62–1.63 | 1.59 |

[a]represents the unleached beads and the core of the leached bead
[b]measured in air
*index of refraction of solid structural component of sheaths.

In a retroreflection application in air, the leached beads exhibited an increase in index of refraction from 1.55 to 1.61, demonstrating that the beads with air filled sheaths (composite bead) exhibit a retroflective behavior indicating an index of refraction higher than that shown by the original unleached beads. The increase in index of refraction also demonstrated optical uniformity of the sheath.

EXAMPLE 26

This example illustrates the post-heat treatment of uniform sheathed ceramic fibers to provide fibers whose sheaths have a refractive index greater than that of the core. Ceramic fibers ($3Al_2O_3:B_2O_3:2SiO_2$) prepared as described in Example 13 were refired at 600° C. to remove any organic materials. The fibers were leached in 9.8% aqueous hydrofluoric acid at room temperature for 20 minutes, rinsed with a distilled water, and dried at 200° C. to yield leached fibers having a diameter of 9 micrometers with a uniform sheath 1.5 micrometers thick.

The leached fibers were then post-fired in air at 1410°–1420° C. for about 1¼ hours. Petrographic examination revealed flexible, strong fibers which appeared to have undergone a slight shrinkage in diameter. The fibers contained needle-shaped, birefringent crystals having a preferred orientation in the core, surrounded by the amorphous skin or sheath. The refractive index Example 13 (0.9 g, 11 micrometers in diameter and having a 2–4 micrometer thick uniform sheath) were infiltrated at room temperature for 1 hour by immersing the fibers in a solution containing 2.22 g of zinc (II) acetate dihydrate, 2.50 g of nickel (II) acetate tetrahydrate, 16.16 g of iron (III) nitrate.9H₂O and 25 ml of distilled water. The fibers were recovered by decantation, rinsed five times with distilled water, and air dried at 100° C. The fibers were then fired at 810° C. in air for 2 hours using a controlled electrical furnace, and 0.92 g of infiltrated fibers were recovered, the fill material having the composition:

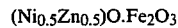

$(Ni_{0.5}Zn_{0.5})O.Fe_2O_3$

Optical analysis of the light brown to brown fibers showed uniform infiltration. The fibers were attracted to a permanent magnet, supported their own weight, and moved about 6.4 mm (¼ inch) in the presence of a magnet. The magnetic moment, measured at 10,000 oersteds, was 4.1 electromagnetic units (emu), and the hysteresis loss was very small.

EXAMPLE 29

This example describes the resistance to thiophene poisoning exhibited by nickel and platinum catalysts that have been introduced into the fibers of the ceramics of the present invention. Alumina-boria-silica fibers, filled with nickel or platinum, prepared according to Example 14, were placed in the injection port of a Hewlett-Packard ® gas chromatograph (Model 5880A) equipped with a 15-meter long OV-1 capillary column. Dodecane, dodecene, and an internal standard (1 part decane/1000 parts hexane) were separated and resolved on the column. The samples were gas chromatographed, and the results of the analyses are summarized in the following Table.

TABLE XVI

| Sample | Catalyst | Elution time (minutes) | Observations |
|---|---|---|---|
| decane[a] | none | 4.4 | control |
| dodecane | none | 7.3 | control |
| dodecene | none | 7.1 | control |
| dodecane | b | 7.3 | dodecane eluted only |
| dodecene | b | 7.1 | dodecene eluted only |
| dodecene | c,d | 7.3 | dodecane eluted; only trace of dodecene remained; no poisoning of catalyst noted |
| dodecene | e,d | 7.3 | some poisoning of catalyst noted; a 25% reduction of dodecene to dodecane obtained |

[a]Internal standard (1 part decane per 1000 parts hexane)
[b]Ceramic fibers not containing catalyst in the injection port.
[c]Ceramic fibers containing platinum in the injection port.
[d]Forty microliters of 1% thiophene in hexane were injected with the sample of dodecene.
[e]Ceramic fibers containing nickel in the injection port.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A fired, non-vitreous, non-fused, monolithic, ceramic article characterized by having a core and a sheath or outer layer, at least a portion of said core being enveloped or covered by said sheath or outer layer, said sheath or outer layer having a structure characterized by interconnected micropores, said micropores having an average diameter of less than 300 Å, said core having a substantially non-porous structure.

2. The article of claim 1 wherein said ceramic article comprises silica and at least one oxide selected from the group consisting of alumina, zirconia, and mixtures thereof.

3. The article of claim 2 wherein said ceramic article further includes at least one oxide selected from the group consisting of boria, chromia, and titania.

4. The article of claim 1 wherein said ceramic article comprises alumina and zirconia.

5. The article of claim 1 wherein said article is in the form of a fiber.

6. The article of claim 5 wherein said fiber is a continuous fiber.

7. The article of claim 5 wherein said fiber is a non-continuous fiber.

8. A fiber-reinforced plastic composite comprising a plastic material and at least one article of claim 5.

9. A fiber-reinforced metal composite comprising a metal matrix and at least one article of claim 5.

10. A woven fabric comprising a plurality of articles of claim 5.

11. A non-woven fabric comprising a plurality of articles of claim 5.

12. The article of claim 1 wherein said article is in the form of a bead.

13. The article of claim 1 wherein said article is in the form of a coating.

14. The article of claim 1 wherein said article is in the form of a solid or hollow spheroid.

15. The article of claim 1 wherein said article is in the form of a flake.

16. The article of claim 1 wherein said article is an unshaped aggregate.

17. The article of claim 1 wherein said article is characterized by having an average sheath or outer layer thickness at least 9 times as great as the average thickness of the core.

18. The article of claim 1 wherein said article is characterized by having an average sheath or outer layer thickness equal to or less than 1/10 as great as the average thickness of the core.

19. The article of claim 1 wherein said article is characterized by having an average sheath or outer layer thickness from 1/10 to 9 times as great as the average thickness of the core.

20. The article of claim 1 wherein said article comprises at least one crystalline or microcrystalline phase.

21. The article of claim 1 wherein said article is transparent.

22. The article of claim 1 wherein said article is reflective.

23. The article of claim 1 wherein said sheath or outer layer is prepared by leaching a ceramic body to separate leachable material from the portion of the body which forms the sheath or outer layer of the article.

24. The article of claim 23 wherein said ceramic body is derived from a sol-gel process.

25. The article of claim 23 wherein said ceramic body is leached by a chemical leachant comprising hydrofluoric acid.

26. The article of claim 25 wherein said leachant is free of water.

27. The article of claim 25 wherein said leachant further comprises an inorganic or an organic acid in addition to hydrofluoric acid.

28. The article of claim 25 wherein said chemical leachant comprises hydrofluoric acid vapor.

29. The article of claim 23 wherein said chemical leachant comprises precursors of hydrofluoric acid.

30. The article of claim 1 wherein said porous sheath or outer layer contains a fill material.

31. The article of claim 30 wherein said sheath or outer layer has an index of refraction different from the index of refraction of said core.

32. The article of claim 30 wherein said fill material is a solid.

33. The article of claim 30 wherein said fill material is a metal, metal oxide, or metal salt.

34. The article of claim 30 wherein said fill material is a catalyst.

35. The article of claim 30 wherein said fill material is a biochemical.

36. The article of claim 30 wherein said fill material comprises a living organism.

37. The article of claim 30 wherein said fill material is organic.

38. The article of claim 37 wherein said fill material is a polymer.

39. The article of claim 30 wherein said fill material is inorganic.

40. The article of claim 30 wherein said fill material is magnetic.

41. The article of claim 30 wherein said fill material is a fluid.

42. The article of claim 30 wherein said fill material is electrically conductive.

43. A woven fabric comprising a plurality of articles of claim 30, each of said articles being in the form of a fiber.

44. A non-woven fabric comprising a plurality of articles of claim 30, each of said articles being in the form of a fiber.

45. The article of claim 1 wherein the ratio of the porosity of the sheath or outer layer to the porosity of the core is at least about 2.5:1.

46. Method of preparing the ceramic article of claim 1 comprising the steps of:
 (1) contacting a ceramic article with a leachant for a sufficient period of time until a sheath or outer layer is formed on the unchanged ceramic core, and
 (2) recovering the leached ceramic article.

47. The method of claim 46 wherein said leachant is hydrofluoric acid.

48. The method of claim 47 wherein said leachant further comprises a mineral acid in addition to hydrofluoric acid.

49. The method of claim 46 wherein said leachant is hydrofluoric acid vapor.

50. The method of claim 46 wherein said leachant comprises precursors of hydrofluoric acid.

51. Method for infiltrating the porous sheath of the ceramic article of claim 1 comprising the steps of:
 (1) treating the ceramic article of claim 1 with an infiltrate,
 (2) recovering the infiltrated ceramic article, and, optionally,
 (3) treating the resultant infiltrated ceramic article.

* * * * *

UNITED STATES PATENT AND TRADEMARK OFFICE
CERTIFICATE OF CORRECTION

PATENT NO. : 4,605,594

DATED : August 12, 1986

INVENTOR(S) : Kenneth E. Owens and Robert A. Hatch

It is certified that error appears in the above-identified patent and that said Letters Patent is hereby corrected as shown below:

Col. 8, line 33, "as as" should read --or as--.

Signed and Sealed this

Fourth Day of November, 1986

[SEAL]

*Attest:*

DONALD J. QUIGG

*Attesting Officer*    *Commissioner of Patents and Trademarks*